(12) United States Patent
Niddam-Hildesheim et al.

(10) Patent No.: US 7,655,796 B2
(45) Date of Patent: *Feb. 2, 2010

(54) PROCESS FOR THE PREPARATION OF ROSUVSTATIN

(75) Inventors: Valerie Niddam-Hildesheim, Ein Vered (IL); Kobi Chen, Ramat HaSharon (IL)

(73) Assignee: Teva Pharmaceutical Industries Ltd., Petah Tiqva (IL)

(*) Notice: Subject to any disclaimer, the term of this patent is extended or adjusted under 35 U.S.C. 154(b) by 259 days.

This patent is subject to a terminal disclaimer.

(21) Appl. No.: 11/704,046

(22) Filed: Feb. 7, 2007

(65) Prior Publication Data

US 2007/0142418 A1 Jun. 21, 2007

Related U.S. Application Data

(63) Continuation of application No. 11/181,968, filed on Jul. 13, 2005, now Pat. No. 7,179,916.

(60) Provisional application No. 60/587,653, filed on Jul. 13, 2004.

(51) Int. Cl.
*C07D 239/42* (2006.01)

(52) U.S. Cl. .................................... 544/297

(58) Field of Classification Search ................ 544/297
See application file for complete search history.

(56) References Cited

U.S. PATENT DOCUMENTS

| | | | |
|---|---|---|---|
| 4,231,938 | A | 11/1980 | Monaghan et al. |
| 4,346,227 | A | 8/1982 | Terahara et al. |
| 4,444,784 | A | 4/1984 | Hoffman et al. |
| 4,739,073 | A | 4/1988 | Kathawala |
| 5,006,530 | A | 4/1991 | Angerbauer et al. |
| 5,177,080 | A | 1/1993 | Angerbauer et al. |
| 5,260,440 | A | 11/1993 | Hirai et al. |
| 5,354,879 | A | 10/1994 | Konoike et al. |
| RE37,314 | E | 8/2001 | Hirai et al. |
| 6,316,460 | B1 | 11/2001 | Creekmore et al. |
| 6,333,198 | B1 | 12/2001 | Edmeades et al. |
| 6,777,552 | B2 | 8/2004 | Niddam-Hildesheim et al. |
| 6,858,618 | B2 | 2/2005 | Raza et al. |
| 7,161,004 | B2 | 1/2007 | Gudipati et al. |
| 2005/0131066 | A1 | 6/2005 | Niddam-Hildesheim et al. |
| 2005/0222415 | A1 | 10/2005 | Kumar et al. |

FOREIGN PATENT DOCUMENTS

| | | |
|---|---|---|
| CN | 1 763 015 | 4/2006 |
| EP | 0 850 902 | 7/1998 |
| EP | 0 521 471 | 10/2000 |
| WO | WO 00/17150 | 3/2000 |
| WO | WO 00/49014 A | 8/2000 |
| WO | WO 01/60804 | 8/2001 |
| WO | WO 03/016317 | 2/2003 |
| WO | WO 03/032995 | 4/2003 |
| WO | WO 03/087112 | 10/2003 |
| WO | WO 03/097614 A | 11/2003 |
| WO | WO 2004/014872 | 2/2004 |
| WO | WO 2004/052867 | 6/2004 |
| WO | WO 2006/100689 | 9/2006 |

OTHER PUBLICATIONS

Anelli, et al., "Fast And Selective Oxidation Of Primary Alcohols To Aldehydes Or To Carboxylic Acids And Of Secondary Alcohols To Ketones Mediated By Oxoammonium Salts Under Two-Phase Conditions", J. Org. Chem., 1987, pp. 2559-2562, vol. 52, No. 12.
Hull, et al., "Quantification Of Rosuvastatin In Human Plasma By Automated Solid-Phase Extraction Using Tandem Mass Spectrometric Detection", Journal of Chromatography B: Biomedical Sciences & Applications, 2002, pp. 219-228, vol. 772, No. 2.
Lenz, et al., "Tetra-N-Propylammonium Perruthenate (TPAP)-Catalysed Oxidations Of Alcohols Using Molecular Oxygen As A Co-Oxidant", J. Chem. Soc., Perkin Trans. 1, 1997, 3291-3292.
Ley, et al., Synthesis, 1994, 639-666.
Lipid Research Clinics Program, "The Lipid Research Clinics Coronary Primary Prevention Trial Results: I. Reduction In Incidence Of Coronary Heart Disease", J.A.M.A., 1984, 351-74, vol. 251, No. 3.
Scandinavian Simvastatin Survival Study Group, "Randomised Trial Of Cholesterol Lowering In 4444 Patients With Coronary Heart Disease: The Scandinavian Survival Study (4s)", The Lancet, 1994, pp. 1383-1389, vol. 344.
Snyder, et al., Introduction To Modern Liquid Chromatography, 2nd ed., John Wiley & Sons: New York, 1979, pp. 549, 552, 571-572.
Strobel, et al., Chemical Instrumentation: A Systematic Approach, 3rd ed., Wiley & Sons: New York, 1989, pp. 391-393, 879, 894, 922, 924-925, 953.
Wantanabe, et al., "Synthesis And Biological Antivity Of Methanesulfonamide Pyramidine-And N-Methanesulfonyl Pyrrole-Substituted 3,5-Dihydroxy-6-Heptenoates, A Novel Series Of HMG-CoA Reductase Inhibitors", Bioorganic & Medicinal Chemistry, 1997, pp. 437-444, vol. 5, No. 2.
Witztum, "Chapter 36: Drugs Used In The Treatment Of Hyperlipoproteinemias", Goodman & Gilman's The Pharmacological Basis Of Therapeutics, 9th ed., pp. 875-897.
Konoike, et al. "Practical Synthesis of Chiral Synthons for the Preparation of HMG-CoA Reductase Inhibitors" J. Org. Chem., vol. 59, 1994, pp. 7849-7854.

*Primary Examiner*—Taofiq A Solola
(74) *Attorney, Agent, or Firm*—Kenyon & Kenyon LLP

(57) ABSTRACT

The present invention provides a process for the preparation of the rosuvastatin intermediate FPP-CHO and its conversion to rosuvastatin and pharmaceutically acceptable salts thereof.

26 Claims, No Drawings

PROCESS FOR THE PREPARATION OF ROSUVSTATIN

CROSS-REFERENCE TO RELATED APPLICATIONS

This application is a continuation of U.S. application Ser. No. 11/181,968, filed Jul. 13, 2005, now U.S. Pat. No. 7,179,916, and claims the benefit of provisional application Ser. No. 60/587,653, filed Jul. 13, 2004, which is incorporated herein by reference.

FIELD OF THE INVENTION

The present invention relates to processes for the preparation of rosuvastatin.

BACKGROUND OF THE INVENTION

Statins are currently the most therapeutically effective drugs available for reducing low-density lipoprotein (LDL) particle concentration in the blood stream of patients at risk for cardiovascular disease. Thus, statins are used in the treatment of hypercholesterolemia, hyperlipoproteinemia, and atherosclerosis. A high level of LDL in the bloodstream has been linked to the formation of coronary lesions that obstruct the flow of blood and can rupture and promote thrombosis (Goodman and Gilman, The Pharmacological Basis of Therapeutics, page 879, 9th Ed. 1996).

Statins inhibit cholesterol biosynthesis in humans by competitively inhibiting the 3-hydroxy-3-methyl-glutaryl-coenzyme A ("HMG-CoA") reductase enzyme. HMG-CoA reductase catalyzes the conversion of HMG to mevalonate, which is the rate determining step in the biosynthesis of cholesterol. Decreased production of cholesterol causes an increase in the number of LDL receptors and corresponding reduction in the concentration of LDL particles in the bloodstream. Reduction in the LDL level in the bloodstream reduces the risk of coronary artery disease (J.A.M.A. 1984, 251, 351-74).

Currently available statins include lovastatin, simvastatin, pravastatin, fluvastatin, cerivastatin and atorvastatin, which are administered in their lactone form, as sodium salts or as calcium salts. Rosuvastatin calcium is disclosed in U.S. Pat. No. 5,260,440.

Rosuvastatin (7-[4-(4-fluorophenyl)-6-isopropyl-2-(N-methyl-N-methylsulfonylamino) pyrimidin-5-yl]-(3R,5S)-dihydroxy-(E)-6-heptenoic acid) calcium is an HMG-CoA reductase inhibitor, developed by Shionogi for the once daily oral treatment of hyperlipidaemia (Ann Rep, Shionogi, 1996; Direct communications, Shonogi, 8 Feb. 1999 & 25 Feb. 2000). Rosuvastatin is a superstatin, which can lower LDL-cholesterol and triglycerides levels more effectively than first generation drugs. Rosuvastatin calcium has the following chemical formula:

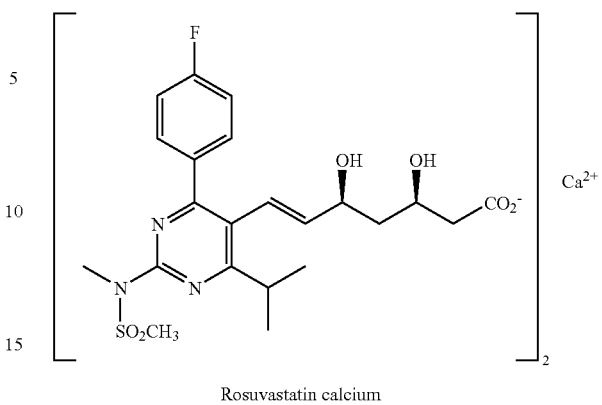

Rosuvastatin calcium

Rosuvastatin calcium is marketed under the name CRESTOR® for treatment of a mammal such as a human. According to the maker of CRESTOR®, it is administered in a daily dose of from about 5 mg to about 40 mg. For patients requiring less aggressive LDL-C reductions or who have pre-disposing factors for myopathy, the 5 mg dose is recommended, while 10 mg dose is recommended for the average patient, 20 mg dose for patients with marked hyper-cholesterolemia and aggressive lipid targets (>190 mg/dL), and the 40 mg dose for patients who have not been responsive to lower doses. WO 03/032995 further discloses a method of preventing dementia by administering rosuvastatin to a patient.

4-(Fluorophenyl)-6-isopropyl-2-(N-methyl-N-methylsulfonylamino)-5-hydroxymethyl-pyrimidine (FPP-OH) is a key intermediate in the synthesis of rosuvastatin. The oxidation of FPP-OH to 4-(Fluorophenyl)-6-isopropyl-2-(N-methyl-N-methylsulfonylamino)-5-formyl-pyrimidine (FPP-CHO) is an important step in the synthesis of rosuvastatin.

EP Patent No. 521,471 and U.S. Pat. No. 5,260,440 disclose the synthesis of rosuvastatin. The oxidation of FPP-OH therein is performed using Tetra Propyl Ammonium Perruthenate (TPAP). Oxidation with TPAP is described in Lenz et al. J. Chem. Soc. PT1, 1997, 3291-3292 and in Ley et al., Synthesis 1994, 639-666. TPAP is an expensive Ruthenium derivative.

There is a need in the art for processes which allow for production of highly pure rosuvastatin in a facile and cost effective manner on an industrial scale.

SUMMARY OF THE INVENTION

In one embodiment the present invention provides a process of preparing FPP-CHO which comprises reacting FPP-OH with Tempo. In one embodiment the present invention provides a process for preparing FPP-CHO comprising the following steps: (a) mixing FPP-OH and 2,2,6,6-tetramethylpiperidine-1-oxyl (Tempo) in an organic solvent to form a reaction mixture; (b) combining the reaction mixture with NaClO; (c) maintaining the mixture for at least about 30 minutes; and (d) recovering the FPP-CHO.

Preferred solvents are ethyl acetate and acetonitrile. In one embodiment, the pH of the NaClO is about 8 to about 9. The pH of the NaClO is adjusted using a base selected from the group consisting of: sodium methoxide, sodium ethoxide, sodium phenoxide, sodium hydroxide, potassium hydroxide, sodium carbonate, potassium carbonate, sodium hydrogencarbonate, potassium hydrogencarbonate and calcium carbonate.

In another embodiment of the present invention, FPP-OH and Tempo are mixed in the presence of a co-oxidant. Inorganic salts, alkali metals, alkaline earth metal bromides, and chloride salts are suitable co-oxidants. In a preferred embodiment of the invention, the co-oxidant is KBr.

In another embodiment, FPP-COH is recovered by precipitation. In one embodiment, the precipitate is slurried and recrystallized. The precipitate is preferably recrystallized from a mixture of water and acetonitrile.

In another embodiment, the present invention provides a process for preparing rosuvastatin, comprising converting FPP-CHO as prepared above to rosuvastatin. In another embodiment, the present invention provides a process for preparing rosuvastatin calcium comprising converting rosuvastatin as prepared above to rosuvastatin calcium. Also provided are pharmaceutical compositions and methods of treatment with a pharmaceutically acceptable salt of rosuvastatin, particularly rosuvastatin calcium.

DETAILED DESCRIPTION OF THE INVENTION

The present invention provides a process of preparing FPP-CHO which comprises reacting FPP-OH with Tempo.

The present invention provides a process for preparing the rosuvastatin intermediate FPP-CHO by the oxidation of FPP-OH in the presence of 2,2,6,6-tetramethylpiperidine-1-oxyl ("Tempo") reagent. The process of the invention results in a high yield of high purity rosuvastatin, thus possibly eliminating further purification steps. The process of the present invention is also efficient and relatively less expensive, and Tempo is less toxic than other reagents, and thus is suitable for use on an industrial scale.

The nitrosyl radical Tempo is used in the oxidation process of primary alcohols to aldehydes or to carboxylic acids and of secondary alcohols to ketones. Tempo, shown below, is described in Anelli et al. JOC 1987, 52 (12), 2559-2562 and Lee et al. Tet. Lett., 1976, 20, 1641-1644.

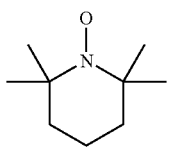

The first embodiment of the invention provides a process for preparing FPP-CHO that includes: (a) mixing FPP-OH and Tempo in an organic solvent to form a reaction mixture; (b) combining the reaction mixture with NaClO; (c) maintaining the reaction mixture for a time sufficient for oxidation of FPP-OH; and (d) recovering FPP-CHO. In the process of the invention, Tempo acts as a catalyst and NaClO acts as an oxidant.

In the process of the first embodiment, Tempo is present in an amount sufficient to catalyze the oxidation of the quantity of FPP-OH used in the reaction to FPP-CHO. The molar ratio of Tempo is preferably about 0.1 to about 0.2 compared to FPP-OH.

The organic solvent may be a suitable solvent such as di-polar aprotic solvents, $C_3$ to $C_7$ esters, $C_2$ to $C_8$ ethers, $C_5$ to $C_7$ aromatic hydrocarbons, and $C_1$ to $C_5$ chlorinated aliphatic hydrocarbons. Preferred organic solvents for use in the first embodiment include, but are not limited to, acetonitrile (ACN), ethyl acetate (EtOAc), Methyl tert-Butyl ether (MTBE), and toluene. More preferably, the organic solvent is acetonitrile or ethyl acetate. The most preferred organic solvent is acetonitrile.

The amount of solvent used depends on the solubility of the reagents. Generally, the amount of solvent is preferably of about 5 ml/g to about 10 ml/g relative to FPP-OH (ml/g).

Oxidation with Tempo is usually performed in methylene chloride, which is a toxic air contaminant. See NIOSH Pocket Guide to Chemical Hazards (DHHS/NIOSH 97-140, 1997) p 208, and Ninth Report on Carcinogens (PB2000-107509, 2000) p III-107. Applicants have found that the solvents listed above, particularly ethyl acetate and acetonitrile, are suitable.

The pH of the NaClO that is combined with the reaction mixture is preferably in the range of about 8 to about 9, and more preferably about 8.6 to about 8.8. The pH may be adjusted using a suitable base, for example, an organic amine, an alkoxide, an alkali metal hydroxide, an alkaline earth metal hydroxide, an alkali metal hydride, an alkaline earth metal hydride or an alkali or alkaline earth metal carbonate or hydrogencarbonate salt. Specific examples of bases include, for example, sodium methoxide, sodium ethoxide, sodium phenoxide, sodium hydroxide, potassium hydroxide, sodium carbonate, potassium carbonate, sodium hydrogencarbonate, potassium hydrogencarbonate, and calcium carbonate.

The reaction mixture is maintained for a time sufficient for oxidation of FPP-OH. The time necessary for oxidation of FPP-OH may depend on reaction scale and mixing procedures, and may easily be determined by one skilled in the art. Preferably, the reaction mixture is maintained for about 30 minutes to about 6 hours. More preferably, the reaction mixture is maintained for about two hours.

Preferably, at least about 90%, more preferably at least about 95% (by weight or mole) conversion of FPP-OH to FPP-CHO is achieved during the reaction.

The process of the present invention is performed at a temperature of about 5° C. to about 40° C.; more preferably, the temperature is in the range of about 5° C. to about 25° C.

The process of the invention may optionally include mixing FPP-OH, the catalyst Tempo, and the oxidant NaClO in the presence of a co-oxidant. The co-oxidant may be an inorganic salt such as an alkaline or an alkaline earth salt, including in complex with a halogen such as bromide or chloride. Preferably, the catalyst is KBr.

The FPP-CHO is preferably isolated by precipitation. The reaction mixture may be stirred or cooled to obtain precipitates. An ideal solvent may be one in which FPP-OH is soluble and FPP-CHO is not soluble, causing precipitation upon formation of FPP-CHO.

The precipitate may further be purified by slurry or additional crystallizations. The slurry is a heterogeneous mixture, and may be maintained, preferably with stirring for a few hours. A slurry in water is performed before crystallization in order to remove all the water soluble salts that could be not washed out at the end of the reaction.

The precipitate may be recrystallized to remove impurities from the final product. Recrystallization may be carried out from a mixture of an organic solvent and water. A preferred organic solvent is acetonitrile. The ratio of water to acetonitrile is preferably about 5% to about 20% by volume. The water is added to make the intermediate somewhat insoluble in acetonitrile, allowing for a more facile recrystallization. The recrystallization may be carried out by heating the mixture to obtain a solution, preferably to a temperature above about 40° C., followed by cooling, preferably to a temperature below about 10° C.

The process may optionally further include a step of washing the precipitated intermediate, at any stage during the process. The obtained FPP-CHO may be washed using a solvent selected from the group consisting of: di-polar aprotic solvents, $C_3$ to $C_8$ esters, $C_2$ to $C_8$ ethers, water, or mixtures thereof. Preferred solvents for washing the product include acetonitrile, ethyl acetate, and MTBE. More preferred solvents for washing are acetonitrile and ethyl acetate, while the most preferred organic solvent for washing is acetonitrile.

The precipitated intermediate may optionally be dried at any stage during the process. The drying may be done by moderate heating (for example, under temperatures of about 40° C. to about 50° C., and more preferably of about 45° C.) under reduced pressure. "Reduced pressure" in the context of the present invention means a pressure of preferably about 10 to about 400 mmHg, and more preferably of about 10 to about 100 mmHg.

After preparation of the intermediate FPP-CHO, the intermediate may be converted to rosuvastatin by conventional means, such as depicted in EP 521,471.

The rosuvastatin obtained may then be converted to a pharmaceutically acceptable salt of rosuvastatin, preferably the calcium salt. Rosuvastatin may be contacted with calcium hydroxide, or with a stronger base such as sodium hydroxide followed by addition of a source of calcium such as calcium chloride.

The pharmaceutical compositions of the present invention contain a pharmaceutically acceptable salt of rosuvastatin, preferably rosuvastatin calcium, in a mixture with at least one pharmaceutically acceptable excipient.

Diluents increase the bulk of a solid pharmaceutical composition, and may make a pharmaceutical dosage form containing the composition easier for the patient and care giver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, Rosuvastatin and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, and aspartame, fructose, mannitol and invert sugar may be added to improve the taste.

Preservatives and chelating agents such as alcohol, sodium benzoate, butylated hydroxyl toluene, butylated hydroxyanisole and ethylenediamine tetraacetic acid may be added at levels safe for ingestion to improve storage stability.

According to the present invention, a liquid composition may also contain a buffer such as guconic acid, lactic acid, citric acid or acetic acid, sodium guconate, sodium lactate, sodium citrate or sodium acetate. Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and losenges, as well as liquid syrups, suspensions and elixirs.

The dosage form of the present invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

The dosage of CRESTOR® may be used as guidance. The oral dosage form of the present invention is preferably in the form of an oral capsule having a dosage of about 5 mg to about 40 mg, more preferably capsules of 5, 10, 20 and 40 mg.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

EXAMPLES

Example 1

(a) A 1 L reactor equipped with a mechanical stirrer and a dropping funnel was charged with 4-(Fluorophenyl)-6-isopropyl-2-(N-methyl-N-methylsulfonylamino)-5-hydroxymethyl-pyrimidine (FPP-OH, 100 g), 2,2,6,6-tetramethylpiperidine-1-oxyl (TEMPO, 0.1 g), KBr (3.4 g), and acetonitrile (700 mL). The mixture was stirred at 5° C., and NaClO$_{(aq)}$ (500 mL, 0.7 M, pH=8.8-9.2 (adjusted with solid NaHCO$_3$)) was added. The mixture was stirred for about 6 hours to obtain a white precipitate.

The white precipitate was collected by filtration, washed with acetonitrile (100 mL) and dried at 45° C. under reduced pressure (99.5 g, 100%).

(b) A 3 L three necked flask equipped with a mechanical stirrer was charged with 4-(Fluorophenyl)-6-isopropyl-2-(N-methyl-N-methylsulfonylamino)-5-formyl-pyrimidine (FPP-CHO, 200 g) and water (2000 mL). The mixture was stirred at about room temperature for 2 hours, filtered, washed with water (200 mL) and dried at 55° C. under reduced pressure (182.5 g, 91.25%).

(c) A 2 L three necked flask equipped with a mechanical stirrer and a condenser was charged with 4-(Fluorophenyl)-6-isopropyl-2-(N-methyl-N-methylsulfonylamino)-5-formyl-pyrimidine (FPP-CHO, 180 g, water triturated), water (180 mL), and acetonitrile (1440 mL). The mixture was stirred at about 76° C.-77° C. (reflux) to obtain a clear solution. The solution was then cooled to about 0° C.-5° C. for 5 hours to obtain white crystals.

The crystallized FPP-CHO was collected by filtration, washed with acetonitrile (50 mL), and dried at 45° C. under reduced pressure (164.2 g, 82%).

Example 2

A 100 mL reactor was charged with 10 g of FPP-OH, 0.01 g of TEMPO, 0.34 g of KBr, and 70 mL of MTBE. The mixture was stirred at about 25° C. NaClO$_{(aq)}$ (100 mL, 0.35M, pH=8.6 (adjusted with solid NaHCO$_3$)) was added to the mixture, which was stirred for 2 hours to obtain a white precipitate of FPP-CHO.

The white crystals of FPP-CHO were collected by filtration, washed with 20 mL MTBE, and then dried at 45° C. under reduced pressure (8.5 g, 85.5%).

Example 3

A 100 mL reactor was charged with 10 g of FPP-OH, 0.01 g of TEMPO, 0.34 g of KBr, and 70 mL of acetonitrile. The mixture was stirred at about 25° C. NaClO$_{(aq)}$ (100 mL, 0.35M, pH=8.6 (adjusted with solid NaHCO$_3$)) was added to the mixture, which was stirred for 2 hours to obtain a white precipitate of FPP-CHO.

The white crystals of FPP-CHO were collected by filtration and washed with 20 mL acetonitrile. The FPP-CHO was triturated with 100 mL water for 1 hour, filtered, and dried at 45° C. under reduced pressure (8.0 g, 80.5%).

Example 4

A 100 mL reactor was charged with 5 g of FPP-OH, 5 mg of TEMPO, 0.17 g of KBr, and 35 mL of ethyl acetate. The mixture was stirred at 25° C. NaClO$_{(aq)}$ (50 mL, 0.35M, pH=8.6 (adjusted with solid NaHCO$_3$)) was added to the mixture, which was stirred for 2 hours to obtain a white precipitate of FPP-CHO.

The white crystals of FPP-CHO were collected by filtration, washed with 20 mL ethyl acetate, and dried at 45° C. under reduced pressure (yield=3.6 g, 72.0%).

Example 5

A 100 mL reactor was charged with 5 g of FPP-OH, 5 mg of TEMPO, 0.17 g of KBr, and 35 mL of toluene. The mixture was stirred at about 25° C. NaClO$_{(aq)}$ (50 mL, 0.35M, pH=8.6 (adjusted with solid NaHCO$_3$)) were added to the mixture, which was stirred for 2 hours to obtain a white precipitate of FPP-CHO. The white crystals of FPP-CHO were collected by filtration, washed with 20 mL toluene, and dried at 45° C. under reduced pressure (3.2 g, 64.0%).

Example 6

A 100 mL reactor was charged with 5 g of FPP-OH, 5 mg of TEMPO, 0.17 g of KBr, and 35 mL of ethyl acetate. The mixture was stirred at about 5° C. NaClO$_{(aq)}$ (50 mL, 0.35M, pH=8.6 (adjusted with solid NaHCO$_3$)) was added to the mixture, which was stirred for 2 hours to obtain a white precipitate of FPP-CHO.

The white crystals of FPP-CHO were collected by filtration, washed with 20 mL ethyl acetate, and dried at 45° C. under reduced pressure (4.4 g, 88.5%).

Example 7

A 100 mL reactor was charged with 5 g of FPP-OH, 5 mg of TEMPO, 0.17 g of KBr, and 35 mL of acetonitrile. The mixture was stirred at 5° C. NaClO$_{(aq)}$ (25 mL, 0.7 M, pH=8.8-8.9 (adjusted with solid NaHCO$_3$)) was added to the mixture, which was stirred for 2 hours to obtain a white precipitate of FPP-CHO.

The white crystals of FPP-CHO were collected by filtration and washed with 20 mL acetonitrile. The FPP-CHO was triturated with 20 mL water for 1 hour, filtered, and dried at 45° C. under reduced pressure (4.0 g, 80.6%).

Example 8

A 100 mL reactor was charged with 5 g of FPP-OH, 5 mg of TEMPO, 0.17 g of KBr, and 35 mL of acetonitrile. The suspension was stirred at 5° C. NaClO$_{(aq)}$ (25 mL, 0.7 M, pH=8.8-8.9 (adjusted with solid NaHCO$_3$)) was added to the mixture, which was stirred for 2 hours to obtain a white precipitate of FPP-CHO.

The white crystals of FPP-CHO were collected by filtration and washed with 20 mL acetonitrile. The FPP-CHO was crystallized using 100 mL acetonitrile, filtered, and dried at 45° C. under reduced pressure (2.9 g, 59.0%).

Abbreviations used below: Me: methyl, Et: ethyl, i-Pr: isopropyl, t-Bu: tert-butyl, Ph: phenyl, THF: tetrahydrofuran.

Conversion of FPP-CHO to Rosuvastatin: (PROPHETIC Example Based on EP 521, 471)

The following illustrates conversion of FPP-CHO to Rosuvastatin. Such a process, as disclosed in EP 521,471, includes:

(1) Dissolving 65 g (164 mmol) of (3R)-3-(tert-butyldimethylsilyloxy)glutaric acid-I—((R)-(−)-mandelic acid ester (this compound can be prepared by the method described on page 10 in the specification of KOKAI 2-250852) in 60 mL of methanol. A solution of sodium methoxide in methanol (310 mL, 28% methanol, 1.6 mol) is added dropwise thereto under a nitrogen atmosphere at 0° C. over a period of 45 minutes at an internal temperature under 7° C. The mixture is stirred at 0° C. for 30 minutes and poured into a mixture of conc. HCl (150 mL), water (300 mL), and methylene chloride (500 mL) being stirred under ice-cooling. The organic layer is collected. The aqueous layer is extracted with 200 ml of methylene chloride, and each organic layer is washed with dilute HCl and then with brine. Each organic layer is collected, dried over anhydrous magnesium sulfate, and evaporated to distill off the solvent to give a half ester compound.

(2) To a solution of the thus obtained half ester compound in 10 ml of ether triethylamine and then ethyl chlorocarboxylate are added dropwise under nitrogen atmosphere at −78° C. The resulting white suspension is stirred at 0° C. for 1 hour and cooled to −78° C. The resulting precipitate is filtered off under nitrogen atmosphere and the filtrate is washed with 15 mL of ether. To a suspension of 1.29 g (3.6 mmol) of methyl bromide triphenylphosphonium in 5 ml of THF butyllithium (1.6M hexane, 2.25 mL, 3.6 mmol) is added dropwise under a nitrogen atmosphere at −78° C. The reaction mixture is stirred at 0° C. for 1 hour and cooled to −78° C. and added dropwise to the solution of the thus obtained active ester compound in ether. The reaction mixture is washed with 5 ml of THF and stirred at 0° C. for 1 hour, and 10 mL of 5% sodium hydrogencarbonate is added thereto. The reaction mixture is stirred for 5 minutes and extracted with ethyl acetate and the organic layer is separated and the remaining aqueous layer is extracted with ethyl acetate. Each organic layer is collected and washed with brine, dried over anhydrous magnesium sulfate and concentrated. The obtained residue is subjected to column chromatography on silica gel eluting with ether-ethyl acetate and crystallized from ether-hexane to give methyl (3R)-3-(tert-butyldimethylsilyloxy)-5-oxo-6-triphenylphosphoranylidene hexanate.

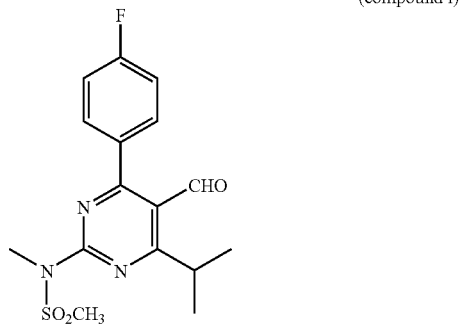

(compound i)

(3) A solution of 190 mg of FPP-OH (compound (i)), 450 mg of methyl (3R)-3-(tert-butyldimethylsilyloxy)-5-oxo-6-triphenylphosphoranylidene hexanate, (prepared in step 2 above) and 5 mL of acetonitrile is refluxed under heating for 14 hours and evaporated under reduced pressure to distill off acetonitrile. The resulting residue is subjected to column chromatography on silica gel eluting with methylene chloride to give 233 mg (Yield: 71.3%) of methyl 7-[4-(4-fluorophenyl)-6-isopropyl-2-(N-methyl-N-methylsulfonylamino)pyrimidin-5-yl)-(3R)-3-(tert-butyldimethylsilyloxy)-5-oxo-(E)-6-heptenate (compound ii) as a syrup.

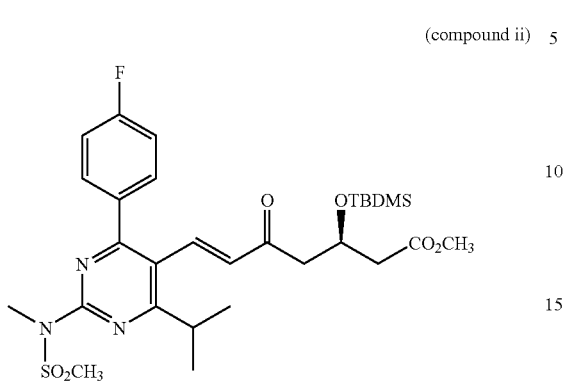

(compound ii)

(4) To a solution of 16 g of compound ii in 100 mL of acetonitrile, a solution of 48% hydrogen fluoride in 400 mL of acetonitrile (1:19) is added dropwise under ice-cooling, and the mixture is warmed to room temperature and stirred for 1.5 hours. The reaction mixture is neutralized with sodium bicarbonate and extracted with ether. The organic layer is washed with sodium chloride, dried, and evaporated under reduced pressure to distill off ether to give 13 g (yield: 100%) of methyl 7-[4-(4-fluorophenyl)-6-isopropyl-2-(N-methyl-N-methylsulfonylamino)pyrimidin-5-yl]-(3R)-3-hydroxy-5-oxo-(E)-6-heptenate (compound iii) as a syrup.

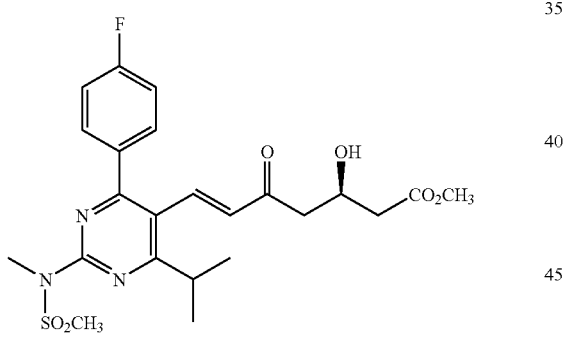

(compound iii)

(5) To a solution of 13 g of compound iii in 350 mL of anhydrous THF and 90 mL of methanol, a solution of 29.7 mL of 1 M diethylmethoxyborane-THF is added at −78° C. The mixture is stirred at the same temperature for 30 minutes. NaBH$_4$ (1.3 g) is added and the mixture is stirred for 3 hours. Acetic acid (16 mL) is added thereto, and the mixture is adjusted to pH 8 with saturated sodium bicarbonate and extracted with ether. The organic layer is washed with water, dried, and the ether is evaporated under reduced pressure. Methanol is added to the resulting residue and the mixture is evaporated three times under reduced pressure. The resulting residue is subjected to column chromatography on silica gel, eluting with methylene chloride/ether (3/1) to give 11.4 g (Yield: 85.2%) of methyl 7-[4-(4-fluorophenyl)-6-iso-propyl-2-(N-methyl-N-methylsulfonylamino)pyrimidin-5-yl]-(3R,5S)-dihydroxy-(E)-6-heptenate (compound iv) as a syrup.

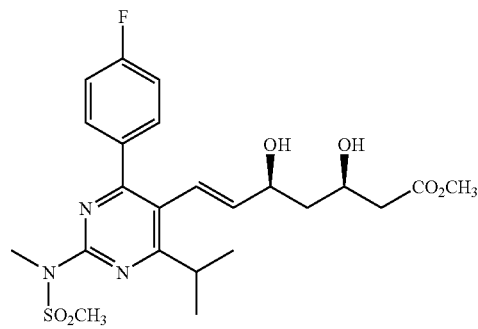

(compound iv)

(6) To a solution of 11.4 g of compound iv in 160 mL of ethanol, sodium hydroxide (0.1 N, 223 mL) is added under ice-cooling. The reaction mixture is warmed to room temperature and stirred for 1 hour. The solvent is distilled off under reduced pressure, and ether is added to the resulting residue. The mixture is stirred to give 11.0 g (Yield: 95.0%) of compound v as powdery crystals.

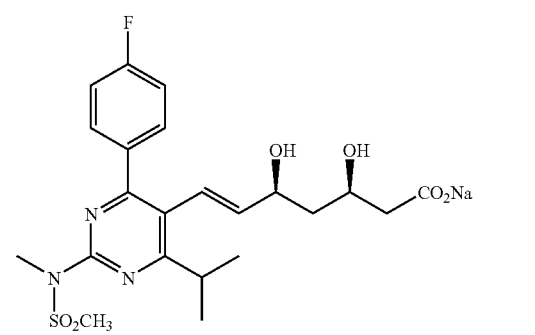

(compound v)

(7) Compound v (1.50 g, 3.00 mmol, sodium salt) is dissolved in 15 mL of water and stirred at room temperature under a nitrogen atmosphere. Successively, 3.00 mL (3.00 mmol) of 1 mol/L calcium chloride is added dropwise thereto over 3 minutes. The reaction mixture is stirred at room temperature for 2 hours, and the resulting precipitate is collected, washed with water, and dried to give 1.32 g of calcium salt as powder. This compound begins to melt at a temperature of 155° C., but the definitive melting point is ambiguous.

What is claimed is:

1. A process of preparing 4-(Fluorophenyl)-6-isopropyl-2-(N-methyl-N-methylsulfonylamino)-5-formyl-pyrimidine (FPP-CHO) comprising the step of reacting 4-(Fluorophenyl)-6-isopropyl-2-(N-methyl-N-methylsulfonylamino)-5-hydroxy-methyl-pyrimidine (FPP-OH) with 2,2,6,6-tetramethylpiperidine-1-oxyl (Tempo).

2. The process of claim 1 comprising the steps of:
    (a) mixing FPP-OH and Tempo in an organic solvent to form a reaction mixture;
    (b) combining the reaction mixture with NaClO;
    (c) maintaining the reaction mixture for a time sufficient to obtain FPP-CHO; and
    (d) recovering FPP-CHO.

3. The process of claim 2, wherein the organic solvent is selected from the group consisting of: di-polar aprotic solvents, $C_3$ to $C_7$ esters, $C_2$ to $C_8$ ethers, $C_5$ to $C_7$ aromatic hydrocarbons, $C_1$ to $C_5$ chlorinated aliphatic hydrocarbons and mixtures thereof.

4. The process of claim 2, wherein the organic solvent is selected from the group consisting of: acetonitrile, ethyl acetate, Methyl tert-Butyl ether (MTBE), toluene, and methylene chloride.

5. The process of claim 2, wherein the organic solvent is acetonitrile or ethyl acetate.

6. The process of claim 2, wherein the amount of solvent is about 5 ml/g to about 10 ml/g per mug of FPP-OH.

7. The process of claim 2, wherein the molar ratio of Tempo to FPP-OH is about 0.1 to about 0.2.

8. The process of claim 2, wherein the reaction mixture is maintained in step (c) for a period of about 30 minutes to about 6 hours.

9. The process of claim 2, wherein the reaction mixture is maintained in step (c) for about 2 hours.

10. The process of claim 2, wherein the reaction mixture is maintained at a temperature of about 5° C. to about 40° C.

11. The process of claim 2, wherein the reaction mixture is maintained at a temperature of about 5° C. to about 25° C.

12. The process of claim 2, wherein at least about 95% of FPP-OH by weight is converted to FPP-CHO.

13. The process of claim 2, wherein the NaClO has a pH of about 8 to about 9.

14. The process of claim 2, wherein the NaClO has a pH of about 8.6 to about 8.8.

15. The process of claim 13, wherein the pH of NaClO is adjusted using a base selected from the group consisting of: an organic amine, an alkoxide, an alkali metal hydroxide, an alkaline earth metal hydroxide, an alkali metal hydride, an alkaline earth metal hydride, an alkali earth metal carbonate, an alkaline earth metal carbonate, and a hydrogen carbonate salt.

16. The process of claim 15, wherein the base is selected from the group consisting of: sodium methoxide, sodium ethoxide, sodium phenoxide, sodium hydroxide, potassium hydroxide, sodium carbonate, potassium carbonate, sodium hydrogencarbonate, potassium hydrogencarbonate and calcium carbonate.

17. The process of claim 2, further comprising the step of drying the recovered FPP-CHO.

18. A process of preparing rosuvastatin or a pharmaceutically acceptable salt of rosuvastatin comprising:
  (a) preparing FPP-CHO according to claim 1; and
  (b) converting the prepared FPP-CHO into rosuvastatin or a pharmaceutically acceptable salt of rosuvastatin.

19. The process of claim 18, wherein step (b) comprises the steps of:
  (a) reacting FPP-CHO with an appropriate substituted side-chain methyl (3R)-3-(tert-butyldimethylsilyloxy)-5-oxo-6-triphenylphosphoranylidene hexanate by Wittig reaction;
  (b) removing the alcohol protecting group;
  (c) reducing the ketone;
  (d) removing the acid protecting group; and
  (e) recovering rosuvastatin or a pharmaceutically acceptable salt of rosuvastatin.

20. A process for preparing a pharmaceutical composition of rosuvastatin or a pharmaceutically acceptable salt thereof comprising combining rosuvastatin prepared according to claim 18 with one or more pharmaceutically acceptable carriers or excipients.

21. The process of claim 20, wherein the pharmaceutically acceptable salt is a calcium salt.

22. A process for preparing rosuvastatin comprising:
  (a) oxidizing FPP-OH with TEMPO to obtain FPP-CHO; and
  (b) converting FPP-CHO to rosuvastatin.

23. The process of claim 2, wherein the step of recovering FPP-CHO is carried out by precipitation.

24. The process of claim 23, further comprising slurrying FPP-CHO in water.

25. The process of claim 23, further comprising recrystallizing FPP-CHO.

26. The process of claim 25, wherein recrystallization is carried out from a mixture of water and acetonitrile.

* * * * *